United States Patent [19]

Michaud

[11] Patent Number: 5,739,090
[45] Date of Patent: Apr. 14, 1998

[54] COMPOSITION BASED ON STABILIZED METHYLENE CHLORIDE WHICH CAN BE USED FOR DEGREASING METALS

[75] Inventor: Pascal Michaud, Saint-Gratien, France

[73] Assignee: Elf Atochem S.A., Puteaux, France

[21] Appl. No.: 584,978

[22] Filed: Jan. 11, 1996

[30] Foreign Application Priority Data

Jan. 10, 1995 [FR] France ................... 95/00194

[51] Int. Cl.⁶ .................... C07C 17/42; C23G 14/02
[52] U.S. Cl. .................... 570/110; 570/116; 510/266; 510/273; 510/256; 510/258
[58] Field of Search .................. 570/110, 116; 510/273, 256, 258, 266

[56] References Cited

U.S. PATENT DOCUMENTS

| 3,646,229 | 2/1972 | Archer et al. | 570/117 |
| 3,670,036 | 6/1972 | Vivian | 570/110 |
| 3,900,524 | 8/1975 | Beckers | 570/109 |
| 4,108,910 | 8/1978 | Godfroid et al. | 570/116 |
| 4,362,573 | 12/1982 | Mackrodt et al. | 134/31 |
| 4,394,284 | 7/1983 | Pryor | 510/273 |

FOREIGN PATENT DOCUMENTS

| 2 268 773 | 1/1975 | France . |
| 2 241 520 | 3/1975 | France . |

OTHER PUBLICATIONS

The Merck Index, 9th Edition, p. 859, Entry No. 6433 (1976).

*Primary Examiner*—C. Warren Ivy
*Assistant Examiner*—Lyman H. Smith
*Attorney, Agent, or Firm*—Millen, White, Zelano, & Branigan, P.C.

[57] ABSTRACT

The invention relates to a composition based on stabilized methylene chloride composed essentially of at least one 1,2-epoxyalkane and of at least one acetal, and no nitroalkane.

The composition according to the invention can be used for degreasing, cleaning and/or drying metal components.

20 Claims, No Drawings

COMPOSITION BASED ON STABILIZED METHYLENE CHLORIDE WHICH CAN BE USED FOR DEGREASING METALS

FIELD OF THE INVENTION

The present invention relates to a composition based on stabilized methylene chloride which can be used for degreasing, cleaning and/or drying metal components.

BACKGROUND OF THE INVENTION

Halogenated hydrocarbons, in particular chlorinated hydrocarbons, by virtue of their solvating power, their non-inflammability and their relatively low boiling point, are used extensively for degreasing metals.

Among the chlorinated hydrocarbons, methylene chloride proves has proven to be particularly stable to oxidation, to hydrolysis and to pyrolysis. Its low boiling point also permits it to be used at low temperatures.

All these properties consequently make it a solvent of choice for degreasing, cleaning and/or drying metal components.

However, when methylene chloride is used in degreasing, cleaning and/or drying some metal components, it can react in particular with aromatic compounds introduced during the machining of the said metal components, e.g., toluene.

This reaction occurs particularly when the said metal components are those made of aluminum or its alloys and those made of magnesium or its alloys.

Without being committed to any one explanation, this reaction is reflected by a more or less significant decomposition of the methylene chloride with the formation, in particular, of acidic compounds such as hydrochloric acid or phosgene.

This decomposition results in a significant decrease in the solvent property of methylene chloride and a significant modification of the pH.

The acid compounds released can additionally corrode the metal components and the plant.

This decomposition is still more marked when methylene chloride is used for hot degreasing or drying operations.

This decomposition of methylene chloride consequently constitutes a serious disadvantage as regards its use as a degreasing, cleaning and/or drying solvent for metal components composed of so-called light metals such as aluminum or magnesium (or their alloys).

Thus, in order to overcome these disadvantages, a great number of compounds have been recommended as inhibitors of the decomposition, or stabilizers, of methylene chloride.

Mention may be made, among the most used compounds, of saturated and unsaturated alcohols, ketones, epoxides, amines, ethers and their mixtures.

Thus, U.S. Pat. No. 3,923,912 recommends the use of methyl ethyl ketone.

U.S. Pat. No. 3,670,036 describes a methylene chloride composition stabilized by:

1 to 10% of a nitroalkane having from 1 to 6 carbon atoms, 0.1 to 5% of an alkylene oxide having from 2 to 4 carbon atoms, and 0 to 10% of a dialkoxyalkane having up to approximately 20 carbon atoms.

Although the use of nitroalkanes introduces a certain preventive effect against the decomposition of methylene chloride in contact with metals, this prevention is very unsatisfactory when it is desired to protect not only the liquid phase but also the vapor phase.

In addition, many compounds mentioned above, used alone or in combination, do not make it possible to pass the very strict long-term stabilization test known as the BAM (Bundesanstadt für Materialprüfung) test.

SUMMARY OF THE INVENTION

A composition based on stabilized methylene chloride has now been found which can be used for degreasing, cleaning, both while cold and while hot, and/or drying metal components, characterized in that it is essentially composed of at least one 1,2-epoxyalkane and of at least one acetal.

As examples of 1,2-epoxyalkanes which can be used according to the present invention, there are included, but not limited to: 1,2-epoxypropane, 1,2-epoxybutane, 1,2-epoxyhexane, 1,2-epoxyoctane and 7-oxabicyclo[4.1.0]heptane, with 1,2-epoxybutane being preferred.

As examples of acetals which can be used according to the present invention, there are included but not limited to: dimethoxymethane, 1,1-dimethoxypropane, 1,1-diethoxybutane, 1,1-dimethoxyhexane, diethoxymethane and 1,3-dioxolane, with dimethoxymethane, commonly known as methylal, being preferred.

According to one aspect of the present invention, use is made of an amount of 1,2-epoxyalkane of between 0.0001% and 16.5% by weight and preferably an amount of between 0.2% and 2% by weight with respect to the total weight of the composition based on methylene chloride.

According to another aspect of the present invention, use is made of an amount of acetal of between 0.55% and 16.50% by weight and preferably an amount of between 0.55% and 3% by weight with respect to the total weight of the composition based on methylene chloride.

The stabilized methylene chloride composition can also contain one or more additives chosen from amines, such as dimethylethylamine, methyldiethylamine or trimethylamine; amino alcohols, such as triethanolamine; ketones, such as acetone or methyl ethyl ketone; nitroalkanes, such as nitromethane or nitropropane; and ethers, such as diethyl ether or tetrahydrofuran.

These additives can be used in amounts of between 0.001% and 5% by weight with respect to the total weight of the methylene chloride composition.

According to another aspect of the invention, the composition contains less than a stabilizing amount of nitroalkane, generally less than about 1% by weight and preferably no nitroalkanes.

The composition according to the invention can be prepared by simply mixing the compounds with methylene chloride.

This mixing can be carried out at room temperature and more especially at a temperature of between 5° C. and 30° C.

The composition according to the invention can be used in particular for degreasing, both while cold and while hot, cleaning and/or drying metal components.

The composition of the invention has the advantage of being a simple composition having exceptional long-term stability. It is also very stable when it is used, in particular for vapor-phase degreasing operations of metal components.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and unless otherwise indicated, all parts and percentages are by weight.

The entire disclosure of all applications, patents and publications, cited above and below, and of corresponding French application 95/00194, filed Jan. 10, 1995, are hereby incorporated by reference.

EXAMPLES

Example 1
(according to the invention)

A methylene chloride composition consisting of 98.37% by weight of $CH_2Cl_2$, 0.63% by weight of 1,2-epoxybutane and 1% by weight of methylal is prepared. This composition is hereinafter denoted by composition (I).

This composition is subjected to the BAM test which comprises the following trials:

Trial 1
The following are added to 25 ml of the composition (I):
25 ml of toluene,
0.175 g of aluminum chloride and
4.5 g of aluminum chaff.
Trial 2
2.5 g of zinc stearate are added to the mixture of Trial 1.
Trial 3
2.5 ml of oleic acid are added to the mixture of Trial 1.

For each trial, the mixtures are brought to 80° C. on a water bath for 18 hours.

300 ml of the composition (I) are then distilled as 3 fractions of approximately 100 ml. Fraction 1 corresponds to the first runnings of the distillation, fraction 2 corresponds to the middle distillation fraction and fraction 3 corresponds to the distillation heel.

25 ml of each fraction are withdrawn and Trial 1 mentioned above is applied while having regard to the amounts shown.

The composition (or the solvent) is accepted as having satisfied the BAM test if there was "no reaction" recorded during each of the six trials considered separately (Trials 1, 2 and 3, and then Trial 1 on fractions 1, 2 and 3).

"No reaction" must be understood to mean no violent exothermic reaction, such as decomposition or explosion.

The results obtained are collected in Table 1.

It is observed that the composition (I) passes the BAM test.

To confirm the ability of the composition (I) to trap hydrochloric acid, the composition (I) was subjected to the test known as "acid acceptance" according to ASTM standard D 2942. The "acid acceptance," measured as equivalent weight of NaOH, is 0.35.

Example 2
(not in accordance with one aspect of the invention)

A methylene chloride composition consisting of 98.87% by weight of methylene chloride, 0.63% by weight of 1,2-epoxybutane and 0.50% by weight of methylal is prepared. This composition is hereinafter denoted by composition (II).

The BAM test is carried out on this composition (II).

The results are reported in Table 1. It is observed that the composition (II) does not pass the BAM test.

A decomposition of fraction 2, which has been subjected to Trial 1, is observed.

TABLE 1

| Compo- | BAM Test | | | | | |
|---|---|---|---|---|---|---|
| | Trial | | | Trial 1 on Fraction | | |
| sition | 1 | 2 | 3 | 1 | 2 | 3 |
| (I) | passed | passed | passed | passed | passed | passed |
| (II) | passed | passed | passed | passed | decomposition | passed |

Example 3

The boiler and the rinsing vessel of a small degreasing machine are filled with equal amounts of the composition (I).

After refluxing for one hour, when the system is in equilibrium, an aliquot is withdrawn from the boiler and from the rinsing vessel.

These two aliquots are analyzed by gas phase chromatography.

The results are collated in Table 2.

TABLE 2

| Constituents of the composition (I) | Percentage by Weight | | |
|---|---|---|---|
| | At the Start | After refluxing for 1 hour in | |
| | | Boiler | Rinsing vessel |
| 1,2-epoxybutane | 0.63 | 1.03 | 0.23 |
| methylal | 1 | 1.20 | 0.80 |

The rinsing vessel is equivalent to the return of the condensates. The results obtained consequently show that the vapor phase is highly stabilized.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. In a method of hot cleaning and degreasing metal components with a composition based on methylene chloride, the improvement wherein said composition also comprises stabilizing amounts of at least one 1,2-epoxyalkane, and at least one acetal, with the provision that the composition is devoid of a nitroalkane.

2. A method according to claim 1, wherein the 1,2-epoxyalkane is 1,2-epoxybutane.

3. A method according to claim 1, wherein the acetal is dimethoxymethane.

4. A method according to claim 2, wherein the acetal is dimethoxymethane.

5. A method according to claim 1, wherein the the amount of 1,2-epoxyalkane is between 0.0001% and 16.50% by weight with respect to the total weight of the composition based on methylene chloride.

6. A method according to claim 5, wherein the amount of 1,2-epoxyalkane is between 0.2% and 2% by weight.

7. A method according to claim 1, wherein the amount of acetal is between 0.55% and 6.50% by weight with respect to the total weight of the composition based on methylene chloride.

8. A method according to claim 5, wherein the amount of acetal is between 0.55% and 6.50% by weight with respect to the total weight of the composition based on methylene chloride.

9. A method according to claim 5, wherein the amount of acetal is between 0.55% and 3% by weight.

10. A method according to claim 5, wherein the 1,2-epoxyalkane is 1,2-epoxybutane.

11. A method according to claim 6, wherein the 1,2-epoxyalkane is 1,2-epoxybutane.

12. A method according to claim 8, wherein the 1,2-epoxyalkane is 1,2-epoxybutane.

13. A method according to claim 7, wherein the acetal is dimethoxymethane.

14. A method according to claim 8, wherein the acetal is dimethoxymethane.

15. A method according to claim 9, wherein the acetal is dimethoxymethane.

16. A method according to claim 12, wherein the acetal is dimethoxymethane.

17. A composition comprising methylene chloride and stabilizing amounts of 1,2-epoxyalkane and an acetal with the provision that the composition is devoid of a nitroalkane.

18. A composition according to claim 17, wherein the 1,2-epoxyalkane is 1,2-epoxybutane.

19. A composition according to claim 18, wherein the acetal is dimethoxymethane.

20. A composition according to claim 19, wherein the amount of 1,2-epoxybutane is 0.2–2% by weight and the amount of dimethoxymethane is 0.55–3% by weight.

* * * * *